United States Patent
Schmitt et al.

(10) Patent No.: US 6,936,734 B2
(45) Date of Patent: Aug. 30, 2005

(54) PROCESS FOR MANUFACTURING UNSATURATED CARBOXYLIC ACID ANHYDRIDES

(75) Inventors: Bardo Schmitt, Mainz (DE); Joachim Knebel, Alsbach (DE); Wolfgang Klesse, Mainz (DE); Andrea Wittkowski, Gross-Umstadt (DE); Benedikt Laux, Monternheim (DE)

(73) Assignee: Roehm GmbH & Co., KG, Darmstadt (DE)

( * ) Notice: Subject to any disclaimer, the term of this patent is extended or adjusted under 35 U.S.C. 154(b) by 158 days.

(21) Appl. No.: 10/068,849

(22) Filed: Feb. 11, 2002

(65) Prior Publication Data

US 2002/0161260 A1 Oct. 31, 2002

(30) Foreign Application Priority Data

Feb. 9, 2001 (DE) .......................................... 101 06 352

(51) Int. Cl.⁷ .......................... C07C 65/00; C07C 51/56
(52) U.S. Cl. ....................................... 562/888; 562/894
(58) Field of Search ................................ 562/888, 894, 562/895

(56) References Cited

U.S. PATENT DOCUMENTS

| 2,319,070 | A | | 5/1943 | Lowe et al. |
|---|---|---|---|---|
| 4,781,868 | A | | 11/1988 | Langerbeins |
| 4,830,789 | A | * | 5/1989 | Hinenoya et al. |
| 4,857,239 | A | * | 8/1989 | Hurtel et al. |
| 4,874,558 | A | | 10/1989 | Fife et al. |

FOREIGN PATENT DOCUMENTS

| DE | 35 44 765 | 6/1987 |
|---|---|---|
| FR | 863 141 | 3/1941 |
| FR | 2 592 040 | 6/1987 |
| GB | 612 790 | 11/1948 |
| WO | WO 95/32940 | 12/1995 |

OTHER PUBLICATIONS

D. Plusquellec, et al., "A New Synthesis of Carboxylic and Carbonic Acid Anhydrides using Phase Transfer Reactions", TETRAHEDRON, vol. 44, No. 9, pp 2471–2476, 1988.

* cited by examiner

Primary Examiner—Michael L. Shippen
Assistant Examiner—Paul A. Zucker
(74) Attorney, Agent, or Firm—Oblon, Spivak, McClelland, Maier & Neustadt, P.C.

(57) ABSTRACT

The present invention relates to a process for preparing an unsaturated carboxylic acid anhydride by reacting an unsaturated carboxylic acid and a lower aliphatic carboxylic acid anhydride in the presence of a stabilizer and catalyst that contains a metal salt of an anionic organic compound which has at least one carboxyl group.

18 Claims, No Drawings

PROCESS FOR MANUFACTURING UNSATURATED CARBOXYLIC ACID ANHYDRIDES

This application is based on German Patent Application DE 10106353.0, filed Feb. 9, 2001, the entire contents of which are hereby incorporated by reference, the same as if set forth in at length.

BACKGROUND OF THE INVENTION

1. Field of the Invention

The invention relates to a process for manufacturing unsaturated carboxylic acid anhydrides, especially the reaction of an unsaturated carboxylic acid with a low molecular weight aliphatic carboxylic acid anhydride.

2. Discussion of the Background

DE 35 10 035 describes a process for the continuous manufacturing of carboxylic acid anhydrides by mixing acetane hydride with a carboxylic acid (the so-called, "re-anhydrization process"). WO 95/32940 describes a process for synthesizing unsaturated carboxylic acid anhydrides, such as, for example, acrylic anhydride or methacrylic anhydride by reacting an aromatic acid chloride, such as, for example, benzoyl chloride, with the anion of the unsaturated carboxylic acid. From an industrial perspective, this process has the drawback that for each mole of anhydride formed, one mole of sodium chloride is formed as a waste product, which then requires safe disposal.

FR 2592040 describes the synthesis of methacrylic anhydride by the reaction of acetic anhydride with methacrylic acid in the absence of a catalyst. The reaction mixture must be stabilized by a polymerization inhibitor.

Many methods are available for manufacturing methacrylic anhydride (MAA). MAA may be obtained from methacrylic acid and the corresponding acid chloride according to WO 9532940, U.S. Pat. No. 4,874,558, or SU 228016. Another synthesizing method is phase transfer catalysis described with the products mentioned above in Lab. Chim. Org., CNRS, Rennes-Beaulieu, France, Tetrahedron (1988), 44(9), 2471-6. DE 35 44 765 describes the carboxylation of methacrylates under metal catalysis at a high temperature and high pressure. MAA can also be manufactured, by way of dehydration of methacrylic acid, with the catalysts $AcOC(CN)_2Me$ (JP 49034655) or $(CN)_2$ plus $Ni(OAc)_2$. A simple synthesis is the reaction of MA and acetic anhydride (AA). In DE 35 10 035, this reaction is described as a continuous process under acid catalysis. FR 2592040 manages entirely without any catalyst in a batch trial.

DE 36 44 222 describes the synthesis of carboxylic acid anhydrides (with incidental mention of AA and others) in the presence of the metal ions Mn, Fe, Co, Ni, and Mg, present as the acetate. These redox metals have a strong tendency to change in the oxidation stage, and this has a negative influence on the progress of the reaction in the case of the synthesis of unsaturated carboxylic acids, and it leads to polymerization.

SUMMARY OF THE INVENTION

One object of the present invention is to provide a process for manufacturing an unsaturated carboxylic acid anhydride which avoids the occurrence of halogen byproducts.

Another object of the present invention is to provide a process for manufacturing an unsaturated carboxylic acid anhydride which improves the reaction time of the re-anhydrization reaction.

Another object of the present invention is to provide a process for manufacturing an unsaturated carboxylic acid anhydride which improves the space-time yield of the re-anhydrization reaction.

Another object of the present invention is to provide a process for manufacturing metbacrylic anhydride which avoids the occurrence of halogen byproducts.

Another object of the present invention is to provide a process for manufacturing methacrylic anhydride which improves the reaction time of the re-anhydrization reaction.

Another object of the present invention is to provide a process for manufacturing methacrylic anhydride which improves the space-time yield of the re-anhydrization reaction.

These and other objects have been achieved by the present invention, the first embodiment of which provides a process for preparing an unsaturated carboxylic acid anhydride, which includes:

reacting an unsaturated carboxylic acid and a lower aliphatic carboxylic acid anhydride in the presence of:
  a catalyst; and
  a stabilizer.

Another embodiment of the present invention provides a process for preparing methacrylic anhydride, which includes:

reacting methacrylic acid and acetic anhydride in the presence of:
  a catalyst; and
  a stabilizer.

BRIEF DESCRIPTION OF THE PREFERRED EMBODIMENTS

A more complete appreciation of the invention and many of the attendant advantages thereof will be readily obtained as the same becomes better understood by reference to the following detailed description of the preferred embodiments of the invention.

A metal salt of an organic compound serves as catalyst. Preferable metals include Cr, Zn, Cu, Ca, Na, Ti, Zr, Hf and La. Mixtures of salts are possible. The organic compound preferably has at least one carboxyl group.

The preferred metal salts used in the present invention do not promote polymerization. The process is thus distinguished in-part from DE 36 44 222 by the use of preferred metal acetates. Preferably, the process is carried out under negative pressure, which is associated with less thermal stress. In addition, the feed process is preferably used, thereby boosting the space-time yield. The reaction is preferably conducted at temperatures ranging from 10° C. to the boiling point of the lower aliphatic acid anhydride. The preferred reagents include unsaturated carboxylic acids (furthermore aromatic carboxyl and aromatic polycarboxylic acids) and lower aliphatic carboxylic acid anhydrides.

The process is preferably carried out at a pressure of 2–20 mbar, which range includes all values and subranges therebetween, including 3, 5, 7, 9, 10, 13, 15 and 17 mbar.

Organic compounds containing at least one carboxyl group preferably mean one or more carboxylic acid salts of lower aliphatic carboxylic acids such as, for example, acetates, propionates, butyrates, laurates, salicylates, etc. and β-diketones such as, for example, acetylacetonates (2,4-pentane dionates), 3,5-heptane dionates, and benzoyl acetonates or β-ketocarboxylic acids such as, for example, acetoacetates or β-ketocarboxylic acid salts such as, for example, ethylacetoacetates or dicarboxylic acids such as, for example, oxalic acid and malonic acid. Metal salts in the form of acetates and acetylacetonates are especially preferred. Mixtures are possible.

The catalyst can be utilized not only for conducting the reaction in the batch reactor but also in reactions conducted according to the feed or continuous process.

When conducting the reaction as a feed process, it is preferable that methacrylic acid and half the acetic anhydride are placed in the reactor in advance, and the other half of the acetic anhydride is added gradually over the course of the reaction.

Preferably, the molar ratio of acetic anhydride to methacrylic acid ranges from 0.5 to 1, with a ratio ranging from 0.55 to 0.65 being more preferred, and a ratio ranging from 0.58 to 0.62 being especially prefered. These ranges include all values and subranges therebetween including 0.51, 0.52, 0.57, 0.6, 0.61, 0.67, 0.7, 0.8, 0.9 and 0.95.

Utilization of the catalyst greatly reduces the reaction time.

The catalyst can easily be separated out because it remains in the reaction as a solid or in solution. The methacrylic anhydride can easily be separated out by distillation, and the reaction solution, while sometimes very strong in color, has no effect on the color of the product obtained.

All conventional inhibitors including, for example, one or more of hydroquinone, hydroquinone monomethyl ether, topanol O, topanol A, phenothiazine, IRGANOX 1010 (registered trade name of the Ciba AG corporation), and N,N'-diphenyl-p-phenylene diamine as well as mixtures thereof, can be used as stabilizers.

The invention preferably relates to a process for manufacturing unsaturated carboxylic acid anhydrides, and more preferably the reaction of an unsaturated carboxylic acid with a lower aliphatic carboxylic acid anhydride, and most preferably, a process for manufacturing methacrylic anhydride by reacting methacrylic acid and acetic anhydride in the presence of a catalyst and a stabilizer.

Preferably, in the process according to the invention, a metal salt is used as the catalyst; Cr, Zn, Cu, Ca, Zr, Ti, Na, La, or Hf is used, either singly or as a mixed salt, as the cation in the metal salt; the anion is an organic compound which has at least one carboxyl group; carboxylic acids, dicarboxylic acids, beta-ketocarboxylic acids, beta-diketones, are used, either singly or in mixtures, as organic anions; and chromium acetate, zirconium acetylacetonate, or titanium acetylacetonate are most preferably used as the catalyst.

An especially preferred embodiment of the present invention provides a process for manufacturing unsaturated carboxylic acid anhydrides, especially the reaction of an unsaturated carboxylic acid with a lower aliphatic carboxylic acid anhydride, and even more preferably, a process for manufacturing methacrylic anhydride by causing methacrylic acid and acetic anhydride to react in the presence of a catalyst and a stabilizer.

EXAMPLES

Having generally described this invention, a further understanding can be obtained by reference to certain specific examples which are provided herein for purposes of illustration only and are not intended to be limiting unless otherwise specified.

Invention Examples

Methacrylic acid, acetic anhydride, and the stabilizers along with the catalyst are put in the reaction flask in advance. The apparatus is evacuated to a pressure of 95 mbar and the contents are heated to the boiling point. Then the distillate containing the acetic acid is drawn off and the second portion of acetic anhydride is added continuously drop by drop.

If the head temperature remains constant, the pressure is slowly reduced till it reaches an ultimate level of approximately 2-20 mbar. Once the reaction has stopped, the contents are cooled to room temperature and the sump is analyzed by GC. The methacrylic anhydride (MAA) content of the crude product is 97-98%. Purity far in excess of 99% can be achieved by fractionated distillation.

| Initial mixture | |
|---|---|
| 322.8 g (3.75 mol) | methacrylic acid (MA) |
| 114.9 g (1.13 mol) | acetic anhydride in advance |
| 114.9 g (1.13 mol) | acetic anhydride added drop by drop |
| 1.61 g (0.5% in terms of MA) | catalyst cf. table |
| 1000 mg (3100 ppm in terms of MA) | phenothiazine |
| 200 mg (620 ppm in terms of MA) | hydroquinone |

Comparison Example

The experiment for purposes of comparison is analogous, but is conducted without adding a catalyst, and is referred to in the table below as the standard initial mixture. In this case, the reaction takes longer than with a catalyst. In addition, the crude product is less pure and the yield is less.

Table of results

Composition of sump

| Example | Reaction time hours | MAA Fl-% | Yield % | Comments/Catalyst |
|---|---|---|---|---|
| Comparison Example | 5.5 | 96.66 | 61.9 | Standard initial mixture, without catalyst |
| 1 | 4.25 | 98.35 | 78.2 | Chromium acetate |
| 2 | 3.5 | 97.1 | 69.2 | Zinc acetate |
| 3 | 3.5 | 97.51 | 70.8 | Copper acetate*monohydrate |
| 4 | 3.5 | 97.14 | 73.9 | Calcium acetate*monohydrate |
| 5 | 4.5 | 96.65 | 72.2 | Sodium acetate |
| 6 | 4.25 | 98.24 | 76.8 | Zirconium acetylacetonate |
| 7 | 4.5 | 96.41 | 65 | Chromium acetylacetonate |
| 8 | 4 | 97.4 | 74.5 | Lanthanum acetylacetonate hydrate |

-continued

Table of results

Composition of sump

| Example | Reaction time hours | MAA FI-% | Yield % | Comments/Catalyst |
|---------|---------------------|----------|---------|-------------------|
| 9 | 4 | 98.56 | 73.5 | Hafnium acetylacetonate |
| 10 | 4.25 | 98.6 | 74.9 | Titanium acetylacetonate |

Obviously, numerous modifications and variations of the present invention are possible in light of the above teachings. It is therefore to be understood that within the scope of the appended claims, the invention may be practiced otherwise than as specifically described herein.

What is claimed is:

1. A process for preparing an unsaturated carboxylic acid anhydride, comprising:
    reacting an unsaturated carboxylic acid and a lower aliphatic carboxylic acid anhydride in the presence of:
    a catalyst wherein said catalyst comprises a metal salt and said metal salt comprises an anionic organic compound which has at least one carboxyl group; and
    a stabilizer,
    wherein said catalst comprises at least one cation selected from the group consisting of Cr, Zn, Ca, Zr, Ti, Na, La, and Hf.

2. The process according to claim 1, wherein said catalyst comprises at least one cation selected from the group consisting of Cr, Zr, Ti, and mixtures thereof.

3. The process according to claim 1, wherein said catalyst comprises a metal salt and said metal salt comprises an anionic organic compound which has at least one group selected from the group consisting of carboxylic acid, dicarboxylic acid, beta-ketocarboxylic acid, beta-diketone and mixtures thereof.

4. The process according to claim 1, wherein said catalyst is selected from the group consisting of chromium acetate, zirconium acetylacetonate, titanium acetylacetonate and mixtures thereof.

5. The process according to claim 1, wherein the unsaturated carboxylic acid anhydride is methacrylic anhydride.

6. The process according to claim 1, wherein the lower aliphatic carboxylic acid anhydride is acetic acid anhydride.

7. The process according to claim 1, wherein the unsaturated carboxylic acid is methacrylic acid.

8. The process according to claim 1, wherein the stabilizer is selected from the group consisting of hydroquinone, hydroquinone monomethyl ether, topanol O, topanol A, phenothiazine, N,N'-diphenyl-p-phenylene diamine, and a mixture thereof.

9. The process according to claim 1, further comprising distilling the unsaturated carboxylic acid anhydride.

10. The process according to claim 1, further comprising separating the catalyst from the unsaturated carboxylic acid anhydride.

11. The process according to claim 1, wherein a molar ratio of the carboxylic acid anhydride to the unsaturated carboxylic acid ranges from 0.5 to 1.

12. The process according to claim 1, wherein a molar ratio of the carboxylic acid anhydride to the unsaturated carboxylic acid ranges from 0.55 to 0.65.

13. A process for preparing methacrylic anhydride, comprising:
    reacting methacrylic acid and acetic anhydride in the presence of:
    a catalyst; and
    a stabilizer,
    wherein said catalyst comprises at least one cation selected from the group consisting of Cr, Zn, Ca, Zr, Ti, Na, La, and Hf.

14. The process according to claim 13, wherein said catalyst comprises a metal salt and said metal salt comprises at least one cation selected from the group consisting of Cr, Zr, Ti, and mixtures thereof.

15. The process according to claim 13, wherein said catalyst comprises a metal salt and said metal salt comprises an anionic organic compound which has at least one carboxyl group.

16. The process according to claim 13, wherein said catalyst comprises a metal salt and said metal salt comprises an anionic organic compound which has at least one group selected from the group consisting of carboxylic acid, dicarboxylic acid, beta-ketocarboxylic acid, beta-diketone and mixtures thereof.

17. The process according to claim 13, wherein said catalyst is selected from the group consisting of chromium acetate, zirconium acetylacetonate, titanium acetylacetonate and mixtures thereof.

18. The process according to claim 13, wherein the stabilizer is selected from the group consisting of hydroquinone, hydroquinone monomethyl ether, topanol O, topanol A, phenothiazine, N,N'-diphenyl-p-phenylene diamine, and a mixture thereof.

* * * * *